US008557251B2

(12) United States Patent
Garcon et al.

(10) Patent No.: US 8,557,251 B2
(45) Date of Patent: Oct. 15, 2013

(54) NON-LIVE TRIVALENT INFLUENZA VACCINE FOR ONE-DOSE INTRADERMAL DELIVERY

(75) Inventors: Nathalie Garcon, Rixensart (BE); Moncef Mohamed Slaoui, Rixensart (BE); Christian Van Hoecke, Rixensart (BE)

(73) Assignee: GlaxoSmithKline Biologicals, SA, Rixensart (BE)

( * ) Notice: Subject to any disclaimer, the term of this patent is extended or adjusted under 35 U.S.C. 154(b) by 731 days.

(21) Appl. No.: 11/762,488

(22) Filed: Jun. 13, 2007

(65) Prior Publication Data

US 2007/0237788 A1 Oct. 11, 2007

Related U.S. Application Data

(63) Continuation of application No. 10/469,191, filed as application No. PCT/EP02/01844 on Feb. 21, 2002, now abandoned.

(30) Foreign Application Priority Data

Feb. 23, 2001 (GB) .................................. 0104538.4
Apr. 3, 2001 (GB) .................................. 0108365.8

(51) Int. Cl.
*A61K 39/145* (2006.01)

(52) U.S. Cl.
USPC ..................................... 424/209.1; 424/210.1

(58) Field of Classification Search
None
See application file for complete search history.

(56) References Cited

U.S. PATENT DOCUMENTS

| | | | |
|---|---|---|---|
| 1,274,081 A | 7/1918 | Riethmueller | |
| 1,436,707 A | 11/1922 | Gaschke | |
| 2,569,901 A | 7/1947 | Richard | |
| 2,559,474 A | 3/1950 | Son | |
| 3,129,708 A | 4/1964 | Krantz | |
| 3,400,715 A | 9/1968 | Pederson | |
| 3,814,097 A | 6/1974 | Ganderton et al. | |
| 3,964,482 A | 6/1976 | Gerstel et al. | |
| 4,724,146 A | 2/1988 | Kino et al. | |
| 4,826,687 A * | 5/1989 | Nerome et al. | 424/450 |
| 4,886,499 A | 12/1989 | Cirelli et al. | |
| 5,080,648 A | 1/1992 | D'Antonio | |
| 5,141,496 A | 8/1992 | Dalto et al. | |
| 5,195,526 A | 3/1993 | Michelson | |
| 5,318,522 A | 6/1994 | D'Antonio | |
| 5,328,483 A | 7/1994 | Jacoby | |
| 5,417,662 A | 5/1995 | Hjertman et al. | |
| 5,569,190 A | 10/1996 | D'Antonio | |
| 5,848,991 A | 12/1998 | Gross et al. | |
| 5,921,963 A | 7/1999 | Erez et al. | |
| 5,997,501 A | 12/1999 | Gross et al. | |
| 6,056,716 A | 5/2000 | D'Antonio et al. | |
| 6,200,291 B1 | 3/2001 | Di Pietro | |
| 6,213,977 B1 | 4/2001 | Hjertman et al. | |
| 6,213,983 B1 | 4/2001 | Cherif-Cheikh | |
| 6,245,532 B1 | 6/2001 | Smith et al. | |
| 6,485,729 B1 | 11/2002 | Smith et al. | |
| 6,494,865 B1 * | 12/2002 | Alchas | 604/192 |
| 6,569,123 B2 | 5/2003 | Alchas et al. | |
| 6,569,143 B2 | 5/2003 | Alchas et al. | |
| 6,623,457 B1 * | 9/2003 | Rosenberg | 604/191 |
| 6,689,118 B2 | 2/2004 | Alchas et al. | |
| 6,776,776 B2 | 8/2004 | Alchas et al. | |
| 6,843,781 B2 | 1/2005 | Alchas et al. | |
| 7,083,599 B2 | 8/2006 | Alchas et al. | |
| 7,223,739 B1 | 5/2007 | Haynes et al. | |
| 2002/0038111 A1 | 3/2002 | Alchas et al. | |
| 2002/0198509 A1 | 12/2002 | Mikszta et al. | |
| 2004/0071734 A1 | 4/2004 | Garcon et al. | |
| 2004/0096463 A1 | 5/2004 | Garcon et al. | |
| 2004/0133160 A1 | 7/2004 | Dalton | |
| 2006/0058736 A1 | 3/2006 | Alchas et al. | |
| 2007/0237788 A1 | 10/2007 | Garcon et al. | |
| 2009/0043280 A1 | 2/2009 | Dalton | |

FOREIGN PATENT DOCUMENTS

| | | |
|---|---|---|
| DE | 4127887 C1 | 1/1993 |
| EP | 0173268 A2 | 3/1986 |
| EP | 0540217 A1 | 10/1992 |
| EP | 0671948 B1 | 8/1997 |
| EP | 0904790 A2 | 3/1999 |
| EP | 1086718 A1 | 3/2001 |
| EP | 1092444 A1 | 4/2001 |
| EP | 1092444 B1 | 5/2006 |
| GB | 2206794 A | 1/1989 |
| JP | 52-132590 | 11/1977 |

(Continued)

OTHER PUBLICATIONS du Chatelet et al (Vaccine 15:449-549, 1997).*
Van Gelder et al (Naval Medical Bulletin 47(1): 197-106, 1947).*
Boger et al (JAMA 165:1687-1689, 1957).*
Clark et al (J. Lab. & Clin. Med. 66(1): 334-341, 1965).*
Phllips et al (Journal of Infectious Diseases 122:26-32, 1970).*
Halperin et al (AJPH 69: 1247-1251, 1979).*
Sanofi Pasteur 314 and 329—VAXIGRIP® Product Monograph, p. 1-25. Jun. 4, 2008.*
Herbert et al. Journal of Infectious Diseases 140:234-238, 1979.*
Tauraso et al. Bulletin World Health Organizint 41:507-516, 1969.*

(Continued)

*Primary Examiner* — Mary E Mosher
(74) *Attorney, Agent, or Firm* — Michael M. Conger

(57) ABSTRACT

The invention relates to the use of a trivalent, non-live influenza antigen preparation, particularly a split influenza preparation, in the manufacture of a one-dose influenza vaccine for intradermal delivery. In particular, the invention relates to the use of split influenza preparations wherein the vaccine comprises at least one non-ionic surfactant selected from the group consisting of the octyl-or nonylphenoxy polyoxyethanols (for example the commercially available Triton™ series), polyoxyethylene sorbitan esters (Tween™ series) and polyoxyethylene ethers or esters of general formula (I): $HO(CH_2CH_2O)_n$-A-R, wherein n is 1-50, A is a bond or —C(O)—, R is $C_{1-50}$ alkyl or phenyl $C_{1-50}$ alkyl; and combinations of two or more of these.

12 Claims, No Drawings

(56) References Cited

FOREIGN PATENT DOCUMENTS

| | | |
|---|---|---|
| JP | 1-13862 B2 | 8/1981 |
| JP | 61-53226 | 3/1986 |
| JP | H07-299143 A | 11/1995 |
| JP | 9-10308 | 1/1997 |
| JP | 2000-37456 A | 2/2000 |
| WO | WO 94/00153 A1 | 1/1994 |
| WO | WO 94/19013 A1 | 9/1994 |
| WO | WO 95/07722 A1 | 3/1995 |
| WO | WO 96/33739 * | 10/1996 |
| WO | WO 98/15287 A1 | 4/1998 |
| WO | WO 99/27986 A1 | 6/1999 |
| WO | WO 99/34850 A1 | 7/1999 |
| WO | WO 00/07530 A1 | 2/2000 |
| WO | WO 00/29016 A1 | 5/2000 |
| WO | WO 00/56358 A2 | 9/2000 |
| WO | WO 00/74763 A2 | 12/2000 |
| WO | WO 01/21151 A1 | 3/2001 |
| WO | WO 01/21152 A1 | 3/2001 |
| WO | WO 01/28613 A1 | 4/2001 |
| WO | WO 02/067983 A1 | 9/2002 |
| WO | WO 02/074336 A2 | 9/2002 |
| WO | WO 02/083214 A1 | 10/2002 |
| WO | WO 02/087494 A2 | 11/2002 |

OTHER PUBLICATIONS

Marks et al. American Review of Respiratory Disease 103:579-581, 1971.*
Payler. British Medical Journal 1977:2:1152 (1977).*
Brown et al. Journal of Infectious Disease 136: s466-s471, 1977.*
Crowe et al. American Journal of Medical Technology 31:387-396, 1965.*
Belshe et al. New England Journal of Medicine 251:2286-94, 2004.*
Kenney et al. New England Journal of Medicine 351:2295-301, 2004.*
Niculescu et al. Arch. Roum. Path. Exp. Microbiol. T. 40 (No. 1): 67-70, 1981.*
De Donato et al. Vaccine 17:3094-3131, 1999.*
Niculescu, et al., "Efficacy of an Adsorbed Trivalent Split Influenza Vaccine Administered by Intradermal Route," Arch. Roum. Path. Exp. Microbiol., T.40(No. 1):67-70 (1931).
Niculescu, et al., "Efficacy of an adsorbed trivalent split influenza vaccine administered by intradermal route." Arch. Roum. Path. Exp. Microbiol., T.40(No. 1):67-70 (1981).
Avison (1937) "Influenza Vaccination." *British Medical Journal*, 358.
Bader (1980) "Influenza Vaccine Experience in Seattle." *American Journal of Public Health*, 70(5): 545.
Baibuk et al. (2000) "Cutaneour vaccination: the skin as an immunologically active tissue and the challenge of antigen delivery." *Journal of Controlled Release*, 66: 199-214.
Belshe et al. (2004) "Serum Antibody Response after Intradermal Vaccination against Influenza." *New England Journal of Medicine*, 351(22): 2286-2294.
Blake (1947) "An Evaluationof Vaccination Against Epidemic Influenza in Man." *Meeting of the NY Academy of Medicine*, 308-328.
Brooks et al. (1977) "Intradermal Administrationof Bivalent and Monovalent Influenza Vaccines." *Annals of Allergy*, 39: 110-112.
Brown et al. (1977) "The Immunizing Effect of Influenza A/New Jersey/ 76 (Hsw1N1) Virus Vaccine Adminstered Intradermally and Intramuscularly to Adults." *Journal of Infectious Diseases*, 136: s466-s471.
Bruyn et al. (1949) "Influenza Vaccine." *American Journal of Diseases in Children*, 77(2): 149-163.
Bruyn et al. (1948) "Influenza Vaccination: A Comparison of Antibody Response Obtained by Verious Methods of Administration." *Journal of Immunology*, 62:1-10.
Chaloupka et al. (1996) "Comparative Analysis of Six European Influenza Vaccines." *European Journal of Clinical Microbiology & Infective Diseases*, 5(2): 121-127.
Chen et al. (2000) "Epidermal immunization by a needle-free powder delivery technology: Immunogenicity of influenza vaccine and protection in mice." *Nature Medicine*, 6(10): 1187-1190.
Cook et al. (2006) "Reactogenicity and immunogenicity of an inactivated influenza vaccine administered by intramuscular or subcutaneous injection in elderly adults." *Vaccine*, 24: 2395-2402.
Crowe (1965) "Experimantal Comparison of Intradermal and Subcutaneous Vaccination With Influenza Vaccine." *American Journal of Medical Technology*, 31(6): 387-396.
Davenport (1979) "The search for the ideal influenza vaccine." *Postgraduate Medical Journal*, 55: 78-86.
Davenport and Hennessy (1960) "Prevention of Influenza in Childhood by Vaccination: Principles, Problems, and Progress." *Viral Infections of Infancy and Childhood*, Chapter 10, pp. 152-155, Hoeber-Harper.
Degano et al. (1998) "Intradermal DNA immunization of mice against influenza A virus using the novel PowerJect® system." *Vaccine*,16(4): 394-398.
Degano et al. (2000) "Gene gun intradermal DNA immunization followed by boosting with modified Vaccinia virus Ankara: en hanced CD8+ T cell immunogenicity and protective efficiency in the influenza and malaria models." *Vaccine* 18: 623-632.
Eaton (1947) "Influenza—A Review of Recent Developments." *California Medicine*, 67(4): 233-237.
Fluzone® Product Insert (1999) Influenza Virus Vaccine USP Trivalent Types A and B (Zonal Purified, Subvirion).
Foy (1970) "Efficacy of Interdermally Administered A2 Hong Kong Vaccine." *Journal of the American Medical Association*, 213(1): 130.
Glazier et al. (1956) "Active Immunization With Influenza Virus A and B in Infants and Children." *Pediatrics*, 17: 482-487.
Grabau (1973) "Comparison of a New Mono-Vacc Tuberculin Test with the Mantoux Test." *CHEST* 63(2): 182-184.
Gross et al. (1981) "Comparison of New Triton X-100- and Tween-Ether-Trated Split-Product Vaccines in Childres." *Journal of Clinical Microbiology*, 14(5): 534-538.
Haensler et al. (1999) "Inradermal DNa immunization by using jet-injectors in mice and monkeys." *Vaccine*, 17: 628-638.
Herbert et al. (1979) "Comparison of Responses to Influenza A/New Jersey/76—A/Victoria/75 Virus Vaccine Administered Intradermally or Subcutaneously to Adults with Chrinic Respiratory Disease." *Journal of Infectious Diseases*, 140(2): 234-238.
Hilleman et al. (1958) "Antibody Response in Volunteers to Asian Influenza Vaccine." *Journal of the American Medical Association*, 166: 1134-1140.
Hunsaker et al. (2001) "Efficacy of intradermal vaccinitation." *Veterinary Immunology and Immunopathology*, 79: 1-13.
Jackson et al. (2001) "Safety and immunogenicity of verying dosages of trivalent inactivated influenza vaccine administered by needle-free jet injectors." *Vaccine*, 19: 4703-4709.
Kenny et al. (2004) "Dose Sparing with Intradermal Injection of Influenza Vaccine." *New England Journal of Medicine*, 351(22): 2295-2301.
Laurent et al. (2007) "Evaluation of the clinical perforamce of a new intradermal vaccine administration technique and associated delivery system." *Vaccine*, 25: 8833-8842.
Lawee et al. (1981) "Efficact of Influenza Inoculation: Intradermal versus Subcutaneous Route." *Canadian Family Physician*, 27: 411-414.
Levine (1988) "Route of administration of influenza vaccine." *Canadian Medical Association Journal*, 138: 200-204.
Majeski (2004) *Duluth News-Tribune* Oct. 27 "Two doctors recommend way to stretch flu vaccine" p. 1-2.
Martin (1942) "Intracutaneous vs. Subcutaueous Vaccination. Comparison of Immunologic Response to Both Methods." *North Carolina Medical Journal*. 3: 492-495.
McCarroll et al. (1958) "Immunization with Asian-Strain Influenza Vaccine." *New England Journal of Medicine*, 259(13): 618-621.
McElroy (1969) "Response to Intradermal Vaccination with $A_2$, Hong Kong Variant, Influenza Vaccine." *New England Journal of Medicine*, 1076.
Montagne et al. (2004) "Intradermal Influenza Vaccination—Can Less Be More?" *New England Journal of Medicine*, 351(22): 2330-2332.

(56) References Cited

OTHER PUBLICATIONS

Nagafuchi et al. (1998) "Intradermal Administration of Viral Vaccines." *Reviews in Medical Virology*, 8: 97-111.
Nanzando Medical Dictionary (1998) 18th Edition, Nanzando, pp. 142, 1304 and 1757 (Partial English translation included.).
Paylor (1977) "Intradermal influenza vaccine using Portojet 19976." *British Medical Journal*, Oct. 29, 1977 p. 1152.
Paylor et al. (1974) "Intradermal Influenza Vaccination." *British Medical Journal*, p. 727.
Rendtorff et al. (1959) "Intradermal Immunization Against Asian Influenza in Children." *Journal of the American Medical Association*, 170: 524-528.
Roberts (1973) "Influenza Vaccination." *British Medical Journal*, Dec. 22, 1973, p. 738.
Ruben (1973) "A new subunit influenza vaccine: acceptability compared with standard vaccines and antigenicity in increasing dosage." *Postgraduate Medical Journal*, 49: 185-192.
Ruddock et al. (1992) "Intradermal Hepatitus B Vaccine." *Canadian Family Physician*, 38: 59-64.
Schneidman (1964) "Reactions to Intradermal Vaccinations." *California Medicine*, 100(4): 287-289.
Stille et al. (1959) "Antibody Response to Intracutaneous and Subcutaneous Influenza Vaccination." *Journal of Laboratory and Clinical Medicine*, 53(5): 751-754.
Struve et al. (1995) "Response to a Booster Dose 18 Months after a Low Anti-HBs Response (10-99 IU/1) to Three Doses of intradermally or Intramuscularly Administered Recombunant Hebatitis B Vaccine." *Infection*, 23(1): 46/42-49/45.
Takiuchi et al. (1998) "Injection Techniques Intradermal Injection." *Rinsho Kango*, 24(13): 1969-1972 (Partial English translation included).
Tauraso (1969) "Effect of Dosage and Route of Inoculation upon Antigenicity of Inactivated Influenza Virus Vaccine (Hong Kong Strain) in Man." *Bulletin of the World Health Organization*, 41: 507-516.
Treanor et al. (2002) "Evaluation of a single dose of half strength inactivated influenza vaccine in healthy adults." *Vaccine*, 20: 1099-1105.
Vaccines (1999) 3$^{rd}$ Edition, pp. 535-537, Plotkin and Orenstien.
Vasil'eva et al. (1987) *Zhurnal Mikrobiologii Epidemiologii I Immunobiologii* 3: 38-42.
Vaxigrip Product Information (2004) Inactivated Influenza Vaccine Trivalent Types A and B (Split Viron).
Vaxigrip Product Information (2008) Inactivated Influenza Vaccine Trivalent Types A and B (Split Viron).
Webster (1999) "Potential Advantages of DNA Immunization for Influenza Epidemic and Pandemic Planning." *Clinical Infectious Diseases*, 28: 225-229.
Weller et al. (1948) "Immunologic Reactions Following the Intradermal Inoculation of Influenza A and B Vaccine." *Proceedings of the Society of Experimental Biology (NY)*, 67: 96-101.
Wong (2005) "Influenza vaccination: options and issues." *Hong Kong Medical Journal*, 11(5): 381-390.
Auewarakul et al, (2007) Vaccine, 25:659-663.
Avison et al, (1973) British Medical Journal, p. 358.
Boger et al, (1957) Journal of the American Med. Assoc., 165(13):1687-1689.
Clark et al, (1965) Journal of Laboratory and Clinical Medicine, 66(1):334-341.
De Donato et al, (1999) Vaccine, 17:3094-3101.
Du Chatelet et al, (1997) Vaccine, 15(4):449-458.
Halperin et al, ( 1979) American Journal of Public Health, 69(12):1247-1251.
Marks et al, (1971) American Review of Respiratory Diseases, 103:579-581.
Phillips et al, (1970) Journal of Infectious Diseases, 122:26-32.
Van Gelder et al, (1947) Naval Medical Bulletin, 47(1):197-206.
US Office Action dated Sep. 29, 2004 for U.S. Appl. No. 10/469,087.
US Office Action dated Feb. 22, 2006 for U.S. Appl. No. 10/469,087.
US Office Action dated Nov. 16, 2006 for U.S. Appl. No. 10/469,087.
US Office Action dated Aug. 16, 2007 for U.S. Appl. No. 10/469,087.
US Office Action dated Nov. 1, 2007 for U.S. Appl. No. 10/469,087.
US Office Action dated Aug. 5, 2008 for U.S. Appl. No. 10/469,087.
US Office Action dated Apr. 30, 2009 for U.S. Appl. No. 10/469,087.
US Office Action dated Apr. 9, 2010 for U.S. Appl. No. 10/469,087.
Wood, et al., "Experience with the clinical development of influenza vaccines for potential pandemics", Med. Microbiol. Immunol., 191:197-201 (2002).
Smith Kline Beecham Meeting Agenda, dated Aug. 31, 2000.
Notice of opposition to a European Patent, dated Apr. 1, 2011. EP Patent No. 1361890 Title: "Influenza Vaccine Formulations for Intradermal Delivery."
Frenck, et al., "Coomparison of the immunogenicity and safety of a split-virion, inactivated, trivalent influenze vaccine (Fluzone) administered by intradermal and intramuscular route in healthy adults, " Vaccine, doi:10.1016/j.vaccine.2011.06.010 (in press, 2011).
Ruben and Jackson, "A New Subunit Influenze Vaccine: Acceptability Compared with Standard Vaccines and Effect of Dose on Antigenicity," J. of Infectious Diseases, 125(6):656-63 (1992).
Office Action mailed Jun. 12, 2011 for U.S. Appl. No. 10/469,087.
Vasilyeva, et al., Antigen-Specific and Antigen-Non-Specific Reactions of the Immunity System After Immunization with Purified and Concentrated Stapylococcal Toxoid, Zhurnal Mikrobiologii Epidemiologii I Immunobiologii, 1987.
Translation summary of Vasilyeva, et al., Summing up the study of the novel preparations of inactivated whole-virion influenza vaccines for protecting children in the USSR, Zhurnal Mikrobiologii Epidemiologii I Immunobiologii, 1987.
Feery et al. "Antibody Response to One and Two Doses of Influenza Virus Subunit Vaccine" The Medical Journal of Australia, Feb. 14, 1976, pp. 186-189.
Howells et al. "Effect of Two Doses of Influenza Vaccine in Stimulating Antibody in Volunteers" The Lancet, Jun. 23, 1973, pp. 1436-1438.
U.S. Appl. No. 60/286,821, Alchas and Garcon.
Beran, et al., "Intradermal influenza vaccination of healthy adults using a new microinjection system: a 3-year randomised controlled safety and immunogenicity trial", BMC Medicine, 7:13, doi 10.1186/1741-7015-7-13 (2009).
Goodwin, et al., "Antibody response to influenza vaccination in the elderly: A quantitative review", Vaccine, 24:1159-69 (2006).
Hehme, et al., "Ten Years of Experience with the Trivalent Split-Influenza Vaccine, Fluarix", Clin. Drug Invest., 22(11)751-769 (2002).
Intanza Package Leaflet: Information for the User, Leaflet last approved Jul. 2011.
Merck Sharp & Dohme Corp, Notice of Opposition against European Patent No. 1 361 890 in the name of Glaxosmithkline Biologicals S.A., filed in Dec. 2011.
SANOFI Pasteur SA, Notice of Opposition against European Patent No. 1 361890B1 in the name of Glaxosmithkline Biologicals S.A., filed in Dec. 2011.
Schevill and Marks, "Adverse reactions to 1975 bivalent influenze vaccine in children", CMA Journal, 116:271 (1977).
Skin Layers/Mantouz Intradermal Injection Scheme.
Weber, Francoise, Declaration, dated Dec. 20, 2011.
Exhibit A of Weber Declaration, European Agency for the Evaluation of Medicinal Products, "Note for Guidance on Harmonisation of Requirements for Influenza Virus", Mar. 12, 1997.
Exhibit E of Weber Declaration, Aventis Pasteur, Clinical Trial Protocol Synopsis GID09 dated Sep. 29, 2004.
Exhibit F of Weber Declaration, Chart.
Weniger, "Influenza Vaccination by Classical Intradermal (ID) route", Centers for Disease Control and Prevention, Intradermal Immunization: An Alternative Route for Vaccine Administration, p. 9, 7-9 Prile 2008.
Final Office Action for U.S. Appl. No. 10/469,087 dated Mar. 12, 2012.
Lina, et al., "A TritonX-split Virion Influenza Vaccine is Safe and Fulfills the Committee for Proprietary Medicinal Products (CPMP) Recommendations for the European Community for Immunogenicity, in Children, Adults and the Elderly", Biologicals, 28:95-103 (2000).
Israeli Pud'd National App'n No. IL84811, dated Feb. 21, 1993, Colb, et al.

* cited by examiner

NON-LIVE TRIVALENT INFLUENZA VACCINE FOR ONE-DOSE INTRADERMAL DELIVERY

CROSS-REFERENCE TO RELATED APPLICATIONS

This application is a continuation application of U.S. application Ser. No. 10/469,191, filed 25 Aug. 2003, now abandoned which is a 371 of International Application No. PCT/EP02/01844, filed 21 Feb. 2002, the contents of which are herein incorporated by reference in their entirety.

FIELD OF THE INVENTION

This invention relates to influenza vaccine formulations for intradermal delivery, methods for preparing them and their use in prophylaxis or therapy. More particularly the invention relates to the use of influenza vaccines which can be administered intraderamally in a single dose to achieve a sufficient immune response to meet regulatory requirements.

BACKGROUND OF THE INVENTION

Influenza virus is one of the most ubiquitous viruses present in the world, affecting both humans and livestock. The economic impact of influenza is significant.

SUMMARY OF THE INVENTION

The influenza virus is an RNA enveloped virus with a particle size of about 125 nm in diameter. It consists basically of an internal nucleocapsid or core of ribonucleic acid (RNA) associated with nucleoprotein, surrounded by a viral envelope with a lipid bilayer structure and external glycoproteins. The inner layer of the viral envelope is composed predominantly of matrix proteins and the outer layer mostly of the host-derived lipid material. The surface glycoproteins neuraminidase (NA) and haemagglutinin (HA) appear as spikes, 10 to 12 nm long, at the surface of the particles. It is these surface proteins, particularly the haemagglutinin, that determine the antigenic specificity of the influenza subtypes.

DETAILED DESCRIPTION OF THE INVENTION

Typical influenza epidemics cause increases in incidence of pneumonia and lower respiratory disease as witnessed by increased rates of hospitalisation or mortality. The elderly or those with underlying chronic diseases are most likely to experience such complications, but young infants also may suffer severe disease. These groups in particular therefore need to be protected.

Currently available influenza vaccines are either inactivated or live attenuated influenza vaccines. Inactivated flu vaccines comprise one of three types of antigen preparation: inactivated whole virus, sub-virions where purified virus particles are disrupted with detergents or other reagents to solubilise the lipid envelope (so-called "split" vaccine) or purified HA and NA (subunit vaccine). These inactivated vaccines are generally given intramuscularly (i.m.).

Influenza vaccines, of all kinds, are usually trivalent vaccines. They generally contain antigens derived from two influenza A virus strains and one influenza B strain. A standard 0.5 ml injectable dose in most cases contains 15 □g of haemagglutinin antigen component from each strain, as measured by single radial immunodiffusion (SRD) (J. M. Wood, et al.: An improved single radial immunodiffusion technique for the assay of influenza haemagglutinin antigen: adaptation for potency determination of inactivated whole virus and subunit vaccines. J. Biol. Stand. 5 (1977) 237-247; J. M. Wood, et al., International collaborative study of single radial diffusion and immunoelectrophoresis techniques for the assay of haemagglutinin antigen of influenza virus. J. Biol. Stand. 9 (1981) 317-330).

In certain circumstances, such as the occurrence of a pandemic influenza strain, it may be desirable to have a vaccine which contains only the single strain. This will help the speed of response to a pandemic situation.

The influenza virus strains to be incorporated into influenza vaccine each season are determined by the World Health Organisation in collaboration with national health authorities and vaccine manufacturers.

Current efforts to control the morbidity and mortality associated with yearly epidemics of influenza are based on the use of intramuscularly administered inactivated influenza vaccines. The efficacy of such vaccines in preventing respiratory disease and influenza complications ranges from 75% in healthy adults to less than 50% in the elderly.

It would be desirable to provide an alternative way of administering influenza vaccines, in particular a way that is pain-free or less painful than i.m. injection, and does not involve the associated negative affect on patient compliance because of "needle fear". It would also be desirable to target the cell mediated immune system for example by targeting the antigen to the dendritic cells and langerhans cells that reside in the skin, particularly in the dermis. Cell mediated immunity appears to assist with viral clearance and recovery from illness and may provide better cross protection between influenza strains than antibodies. It has also been described in the literature that intradermal administration allows for the induction of a mucosal immunity at the level of the mucosal surfaces. This offers a benefit compared to the parental route for a vaccine against a pathogen such as influenza where the portal of entry of the virus is through the nasal route. Thus the mucosal surfaces, initially in the upper respiratory tract, offer the first line of defence.

Furthermore, it would be desirable to reduce the amount of antigen needed for a dose of influenza vaccine. Influenza vaccines are often in short supply.

Experimental intradermal exposure of humans to inactivated influenza vaccines dates back as far as the 1940s. Although the benefits of intradermal vaccination have long been recognised, there has to date been no consensus view that regular vaccination for influenza would be effective and practicable via the intradermal route.

Crowe (1965) Am J Medical Technology 31, 387-396 describes a study comparing intradermal and subcutaneous vaccination with a split influenza vaccine. Two doses of 0.1 ml of vaccine were administered intradermally, 14 days apart. The results obtained for intradermal delivery did not meet the standards set for two of the three strains tested, either after one or after two doses.

McElroy (1969) in New Eng J of Medicine, 6 November, page 1076 describes the administration of a monovalent A strain vaccine intradermally in two doses and suggests that the intradermal route might be considered when vaccine is scarce e.g. when a new, unexpected strain arises.

Tauraso, et al., (1969) Bull Wld Hlth Org 41, 507-516 describe a study using monovalent, whole inactivated influenza vaccine administered subcutaneously (0.25 ml or 0.5 ml) or intradermally (0.1 ml). A booster inoculation was given. The results suggest intradermal delivery is a reasonable alternative to subcutaneous delivery, but the authors suggest that two doses are necessary.

Foy (1970) in a letter to JAMA, Jul. 6, 1970, vol 213 page 130, discusses an experiment to test intradermally administered flu vaccine under natural challenge. Two doses of vaccine were given, three to four weeks apart. The data apparently suggested that intradermal vaccination did prevent disease, but were not conclusive.

In a letter to the British Medical Journal, Oct. 29, 1977 page 1152, an experiment using a jet gun to deliver 0.15 ml of monovalent influenza vaccine intradermally was described with unfavourable results. Intradermal administration was described as requiring further work.

Other authors have pointed out that intradermal injection carries with it the risk of leakage, as does subcutaneous injection. However, because of the small volume of vaccine used in intradermal administration, leakage might result in little or no protection being conferred.

Brooks, et al., (1977) Annals of Allergy 39, 110-112 describe a study in which killed influenza vaccine containing two A strains (40 CCA units of each) and separately a B strain (100 CCA units) was administered intradermally in a 0.1 ml volume. The authors concluded that the intradermal route was feasible and effective for immunisation but that larger doses than can be given intradermally may be required for certain strains.

Brown, et al., (1977) J Infectious Disease 136, 466-471 describe intradermal administration of a formalin-inactivated, whole monovalent influenza A strain vaccine. 40 CCA were used in a 0.1 ml volume. This was compared to intramuscular administration of 0.5 ml (200 CCA). The response to intradermal vaccination was found to be age-dependent and lower than for i.m. vaccination for those with preexisting antibody. The conclusion was that with the vaccination doses used in this study, intradermal vaccination should only be used in special circumstances.

Halperin, et al., (1979) AJPH 89, 1247-1252 describe a comparison of intradermal and subcutaneous routes of influenza vaccination with a bivalent split virus vaccine. 0.1 ml of vaccine containing 40 CCA of each strain was used for the i.d. vaccination.

Herbert and Larke (1979) J Infectious Diseases 140, 234-238 describe a comparison of intradermal and subcutaneous influenza vaccination using a bivalent whole virus vaccine. The intradermal route was found to be less effective than the subcutaneous route where there was little or no previous exposure to the vaccine strain. The authors also observed no advantage in the smaller antigenic mass of the intradermal inoculum in relation to reactogenicity, since this did not appear to reduce side effects from the vaccine that occur with the higher dose subcutaneous immunisation.

Bader (1980) in a letter to AJPH, vol. 70 no. 5 discusses the results of various trials with intradermal delivery of flu vaccine and supports the potential value of intradermal delivery when two doses are given two weeks apart.

Niculescu, et al., (1981) in Arch Roum Path Exp Microbiol, 40, 67-70 describe intradermal administration of a split trivalent vaccine using a "gun-jet injector". Two doses were given, one month apart. The authors conclude that this method of administration can be used to decrease the rate of disease during influenza epidemics.

Thus, the literature shows an interest in intradermal vaccination between the mid-sixties (or earlier) and the early 1980s. However, the prevailing view appears to have been that two doses of vaccine would be needed. Also, there was a widely held view that due to the difficulty of administration and the lack of certainty that the low volume of vaccine would successfully be located in the desired region, the use of the intradermal delivery route would be considered only when rapid and mass vaccination was required e.g. in response to a widespread epidemic. Interestingly, there is little mention of intradermal flu vaccination in the literature since the early eighties. Since the early eighties there has been little mention of intradermal flu vaccination using a protein antigen approach in the literature. Protein efforts appear to have fallen out of favour and attention was turned instead to DNA vaccination. See review by Webster R. G. (1999) in Clin Infect Dis, 28, 225-229 and publications such as Degano, et al., (1999) Vaccine 18, 623-32; Haensler, et al., (1999) Vaccine 17, 628-638; Degano, et al., (1998) Vaccine 16, 394-398.

Thus, the commercially available influenza vaccines remain the intramuscularly administered split or subunit intramuscular vaccines. These vaccines are prepared by disrupting the virus particle, generally with an organic solvent or a detergent, and separating or purifying the viral proteins to varying extents. Split vaccines are prepared by fragmentation of whole influenza virus, either infectious or inactivated, with solubilizing concentrations of organic solvents or detergents and subsequent removal of the solubilizing agent and some or most of the viral lipid material. Split vaccines generally contain contaminating matrix protein and nucleoprotein and sometimes lipid, as well as the membrane envelope proteins. Split vaccines will usually contain most or all of the virus structural proteins although not necessarily in the same proportions as they occur in the whole virus. Subunit vaccines on the other hand consist essentially of highly purified viral surface proteins, haemagglutinin and neuraminidase, which are the surface proteins responsible for eliciting the desired virus neutralising antibodies upon vaccination. Matrix and nucleoproteins are either not detectable or barely detectable in subunit vaccines.

Standards are applied internationally to measure the efficacy of influenza vaccines. The European Union official criteria for an effective vaccine against influenza are set out in the table below. Theoretically, to meet the European Union requirements, an influenza vaccine has to meet only one of the criteria in the table, for all strains of influenza included in the vaccine. However in practice, at least two or more probably all three of the criteria will need to be met for all strains, particularly for a new vaccine such as a new intradermal vaccine. Under some circumstances two criteria may be sufficient. For example, it may be acceptable for two of the three criteria to be met by all strains while the third criterion is met by some but not all strains (e.g. two out of three strains). The requirements are different for adult populations (18-60 years) and elderly populations (>60 years).

|  | 18-60 years | >60 years |
| --- | --- | --- |
| Seroconversion rate* | >40% | >30% |
| Conversion factor** | >2.5 | >2.0 |
| Protection rate*** | >70% | >60% |

*Seroconversion rate is defined as the percentage of vaccinees who have at least a 4-fold increase in serum haemagglutinin inhibition (HI) titres after vaccination, for each vaccine strain.
**Conversion factor is defined as the fold increase in serum HI geometric mean titres (GMTs) after vaccination, for each vaccine strain.
***Protection rate is defined as the percentage of vaccinees with a serum HI titre equal to or greater than 1:40 after vaccination (for each vaccine strain) and is normally accepted as indicating protection.

For an intradermal flu vaccine to be commercially useful it will not only need to meet those standards, but also in practice it will need to be at least as efficacious as the currently available intramuscular vaccines. It will also need to be produced by an acceptable process and will of course need to be commercially viable in terms of the amount of antigen and the number of administrations required. Furthermore, it will need to be administered using a procedure which is reliable and straightforward for medical staff to carry out.

Although intradermal flu vaccines based on inactivated virus have been studied in previous years, the fact that no intradermal flu vaccine is currently on the market reflects the difficulty to achieve effective vaccination via this route.

It has now been discovered that certain trivalent influenza vaccines make particularly good intradermal vaccines which are commercially viable. In particular, a single intradermal administration of such an influenza virus vaccine preparation stimulates systemic immunity at a protective level with a low dose of antigen. Furthermore, the international criteria for an effective flu vaccine are met. More specifically, intradermal administration of the low antigen dose vaccine can produce a systemic seroconversion (4-fold increase in anti-HA titres) equivalent to that obtained by s.c. administration of the same vaccine.

As used herein, the term "intradermal delivery" means delivery of the vaccine to the dermis in the skin. However, the vaccine will not necessarily be located exclusively in the dermis. The dermis is the layer in the skin located between about 1.0 and about 2.0 mm from the surface in human skin, but there is a certain amount of variation between individuals and in different parts of the body. In general, it can be expected to reach the dermis by going 1.5 mm below the surface of the skin. The dermis is located between the stratum corneum and the epidermis at the surface and the subcutaneous layer below. Depending on the mode of delivery, the vaccine may ultimately be located solely or primarily within the dermis, or it may ultimately be distributed within the epidermis and the dermis.

The invention provides in a first aspect the use of a trivalent, non-live influenza antigen preparation in the manufacture of a one-dose influenza vaccine for intradermal delivery. The influenza antigen preparation may be produced according to a variety of known methods, including in particular methods described herein. Preferably the non-live antigen preparation is a split influenza preparation or a subunit antigen preparation prepared from live virus. Most preferably the antigen is a split virus preparation.

The trivalent vaccine according to the invention meets some or all of the EU criteria for influenza vaccines as set out hereinabove, such that the vaccine is capable of being approved for marketing in Europe. Preferably, at least two out of the three EU criteria are met, for the or all strains of influenza represented in the vaccine. More preferably, at least two criteria are met for all strains and the third criterion is met by all strains or at least by all but one of the strains. Most preferably, all strains present meet all three of the criteria.

Preferably the intradermal vaccine described herein comprises at least one non-ionic surfactant which may be selected from the group consisting of the octyl-or nonylphenoxy polyoxyethanols (for example the commercially available Triton™ series), polyoxyethylene sorbitan esters (Tween™ series) and polyoxyethylene ethers or esters of general formula (I):

$$HO(CH_2CH_2O)_n\text{-}A\text{-}R \quad (I)$$

wherein n is 1-50, A is a bond or —C(O)—, R is $C_{1-50}$ alkyl or phenyl $C_{1-50}$ alkyl; and combinations of two or more of these.

Preferred is a combination of two non-ionic surfactants, one from each of the octylphenoxy polyoxyethanols and the polyoxyethylene sorbitan esters, in particular a combination of Tween 80 and Triton X-100. Further possible and preferred combinations of detergents are discussed herein below.

The vaccine according to the invention has a lower quantity of haemagglutinin than conventional vaccines and is administered in a lower volume. Preferably the quantity of haemagglutinin per strain of influenza is about 1-7.5 µg, more preferably approximately 3 µg or approximately 5 µg, which is about one fifth or one third, respectively, of the dose of haemagglutinin used in conventional vaccines for intramuscular administration.

Preferably the volume of a dose of vaccine according to the invention is between 0.025 ml and 2.5 ml, more preferably approximately 0.1 ml or approximately 0.2 ml. A 50 µl dose volume might also be considered. A 0.1 ml dose is approximately one fifth of the volume of a conventional intramuscular flu vaccine dose. The volume of liquid that can be administered intradermally depends in part upon the site of the injection. For example, for an injection in the deltoid region, 0.1 ml is the maximum preferred volume whereas in the lumbar region a large volume e.g. about 0.2 ml can be given.

Suitable non-live flu antigen preparations for use in the invention include an influenza antigen preparation obtainable by the following process:
  (i) harvesting of virus-containing material from a culture;
  (ii) clarification of the harvested material to remove non-virus material;
  (iii) concentration of the harvested virus;
  (iv) a further step to separate whole virus from non-virus material;
  (v) splitting of the whole virus using a suitable splitting agent in a density gradient centrifugation step;
  (vi) filtration to remove undesired materials;
wherein the steps are performed in that order but not necessarily consecutively.

Preferably the virus is grown on eggs, more particularly on embryonated hen eggs, in which case the harvested material is allantoic fluid.

Preferably the clarification step is performed by centrifugation at a moderate speed. Alternatively a filtration step may be used for example with a 0.2 µm membrane. The clarification step gets rid of the bulk of the egg-derived material.

Preferably the concentration step employs an adsorption method, most preferably using $CaHPO_4$. Alternatively filtration may be used, for example ultrafiltration.

Preferably the further separation step (iv) is a zonal centrifugation separation, particularly one using a sucrose gradient. Optionally the gradient contains a preservative to prevent microbial growth.

Preferably the splitting step is performed in a further sucrose gradient, wherein the sucrose gradient contains the splitting agent.

Preferably the filtration step (vi) is an ultrafiltration step which concentrates the split virus material.

Preferably there is at least one sterile filtration step, optionally at the end of the process.

Optionally there is an inactivation step prior to the final filtration step.

Preferably the vaccines according to the invention are administered to a location between about 1.0 mm and 2.0 mm below the surface of the skin. More preferably the vaccine is delivered to a distance of about 1.5 mm below the surface of the skin.

The vaccine to which the invention relates is a split virion vaccine comprising particles. Preferably the vaccine contains particles having a mean particle size below 200 nm, more preferably between 50 and 180 nm, most preferably between 100 and 150 nm, as measured using a dynamic light scattering method (Malvern Zeta Sizer). Particle size may vary from season to season depending on the strains.

Preferred surfactants falling within formula (I) herein are molecules in which n is 4-24, more preferably 6-12, and most preferably 9; the R component is $C_{1-50}$, preferably $C_4$-$C_{20}$ alkyl and most preferably $C_{12}$ alkyl.

Octylphenoxy polyoxyethanols and polyoxyethylene sorbitan esters are described in "Surfactant systems" Eds: Attwood and Florence (1983, Chapman and Hall). Octylphenoxy polyoxyethanols (the octoxynols), including t-octylphenoxypolyethoxyethanol (Triton X-100 ™) are also described in Merck Index Entry 6858 (Page 1162, 12th Edition, Merck & Co. Inc., Whitehouse Station, N.J., USA; ISBN 0911910-12-3). The polyoxyethylene sorbitan esters, including polyoxyethylene sorbitan monooleate (Tween 80 ™) are described in Merck Index Entry 7742 (Page 1308, 12th Edition, Merck & Co. Inc., Whitehouse Station, N.J., USA; ISBN 0911910-12-3). Both may be manufactured using methods described therein, or purchased from commercial sources such as Sigma Inc.

Particularly preferred non-ionic surfactants include Triton X-45, t-octylphenoxy polyethoxyethanol (Triton X-100), Triton X-102, Triton X-114, Triton X-165, Triton X-205, Triton X-305, Triton N-57, Triton N-101, Triton N-128, Breij 35, polyoxyethylene-9-lauryl ether (laureth 9) and polyoxyethylene-9-stearyl ether (steareth 9). Triton X-100 and laureth 9 are particularly preferred. Also particularly preferred is the polyoxyethylene sorbitan ester, polyoxyethylene sorbitan monooleate (Tween 80™).

Further suitable polyoxyethylene ethers of general formula (I) are selected from the following group: polyoxyethylene-8-stearyl ether, polyoxyethylene-4-lauryl ether, polyoxyethylene-35-lauryl ether, and polyoxyethylene-23-lauryl ether.

Alternative terms or names for polyoxyethylene lauryl ether are disclosed in the CAS registry. The CAS registry number of polyoxyethylene-9 lauryl ether is: 9002-92-0. Polyoxyethylene ethers such as polyoxyethylene lauryl ether are described in the Merck index (12th ed: entry 7717, Merck & Co. Inc., Whitehouse Station, N.J., USA; ISBN 0911910-12-3). Laureth 9 is formed by reacting ethylene oxide with dodecyl alcohol, and has an average of nine ethylene oxide units.

The ratio of the length of the polyoxyethylene section to the length of the alkyl chain in the surfactant (i.e. the ratio of n: alkyl chain length), affects the solubility of this class of surfactant in an aqueous medium. Thus, the surfactants of the present invention may be in solution or may form particulate structures such as micelles or vesicles. As a solution, the surfactants of the present invention are safe, easily sterilisable, simple to administer, and may be manufactured in a simple fashion without the GMP and QC issues associated with the formation of uniform particulate structures. Some polyoxyethylene ethers, such as laureth 9, are capable of forming non-vesicular solutions. However, polyoxyethylene-8 palmitoyl ether ($C_{18}E_8$) is capable of forming vesicles. Accordingly, vesicles of polyoxyethylene-8 palmitoyl ether in combination with at least one additional non-ionic surfactant, can be employed in the formulations of the present invention.

Preferably, the polyoxyethylene ether used in the formulations of the present invention has haemolytic activity. The haemolytic activity of a polyoxyethylene ether may be measured in vitro, with reference to the following assay, and is as expressed as the highest concentration of the surfactant which fails to cause lysis of the red blood cells:

1. Fresh blood from guinea pigs is washed with phosphate buffered saline (PBS) 3 times in a desk-top centrifuge. After re-suspension to the original volume the blood is further diluted 10 fold in PBS.
2. 50 µl of this blood suspension is added to 800 µl of PBS containing two-fold dilutions of detergent.
3. After 8 hours the haemolysis is assessed visually or by measuring the optical density of the supernatant. The presence of a red supernatant, which absorbs light at 570 nm indicates the presence of haemolysis.
4. The results are expressed as the concentration of the first detergent dilution at which hemolysis no longer occurs.

Within the inherent experimental variability of such a biological assay, the polyoxyethylene ethers, or surfactants of general formula (I), of the present invention preferably have a haemolytic activity, of approximately between 0.5-0.0001%, more preferably between 0.05-0.0001%, even more preferably between 0.005-0.0001%, and most preferably between 0.003-0.0004%. Ideally, said polyoxyethylene ethers or esters should have a haemolytic activity similar (i.e. within a ten-fold difference) to that of either polyoxyethylene-9 lauryl ether or polyoxyethylene-8 stearyl ether.

Two or more non-ionic surfactants from the different groups of surfactants described may be present in the vaccine formulation described herein. In particular, a combination of a polyoxyethylene sorbitan ester such as polyoxyethylene sorbitan monooleate (Tween 80™) and an octoxynol such as t-octylphenoxypolyethoxyethanol (Triton) X100™ is preferred. Another particularly preferred combination of non-ionic surfactants comprises laureth 9 plus a polyoxyethylene sorbitan ester or an octoxynol ester.

Preferably the or each non-ionic surfactant is present in the final vaccine formulation at a concentration of between 0.001 to 20%, more preferably 0.01 to 10%, and most preferably up to about 2% (w/v). Where one or two surfactants are present, these are generally present in the final formulation at a concentration of up to about 2% each, typically at a concentration of up to about 0.6% each. One or more additional surfactants may be present, generally up to a concentration of about 1% each and typically in traces up to about 0.2% or 0.1% each. Any mixture of surfactants may be present in the vaccine formulations according to the invention.

Non-ionic surfactants such as those discussed above have preferred concentrations in the final vaccine composition as follows: polyoxyethylene sorbitan esters such as Tween 80™: 0.01 to 1%, most preferably about 0.1% (w/v); octyl-or nonylphenoxy polyoxyethanols such as Triton X-100™ or other detergents in the Triton series: 0.001 to 0.1%, most preferably 0.005 to 0.02% (w/v); polyoxyethylene ethers of general formula (I) such as laureth 9: 0.1 to 20%, preferably 0.1 to 10% and most preferably 0.1 to 1% or about 0.5% (w/v).

Other reagents may also be present in the formulation. As such the formulations of the present invention may also comprise a bile acid or a derivative thereof, in particular in the form of a salt. These include derivatives of cholic acid and salts thereof, in particular sodium salts of cholic acid or cholic acid derivatives. Examples of bile acids and derivatives thereof include cholic acid, deoxycholic acid, chenodeoxycholic acid, lithocholic acid, ursodeoxycholic acid, hyodeoxycholic acid and derivatives such as glyco-, tauro-, amidopropyl-1-propanesulfonic-, amidopropyl-2-hydroxy-1-propanesulfonic derivatives of the aforementioned bile acids, or N,N-bis (3Dgluconoamidopropyl) deoxycholamide. A particularly preferred example is sodium deoxycholate (Na-DOC) which may be present in the final vaccine dose.

The vaccine formulation according to the invention preferably comprises a split flu virus preparation in combination with one or more non-ionic surfactants. The one or more non-ionic surfactants may be residual from the process by which the split flu antigen preparation is produced, and/or added to the antigen preparation later. The concentration of the or each non-ionic surfactant may be adjusted to the desired level at the end of the splitting/purification process. It is believed that the split flu antigen material may be stabilised in the presence of a non-ionic surfactant, though it will be understood that the invention does not depend upon this necessarily being the case.

The vaccine according to the invention may further comprise an adjuvant or immunostimulant such as but not limited to detoxified lipid A from any source and non-toxic derivatives of lipid A, saponins and other reagents capable of stimulating a TH1 type response.

It has long been known that enterobacterial lipopolysaccharide (LPS) is a potent stimulator of the immune system, although its use in adjuvants has been curtailed by its toxic effects. A non-toxic derivative of LPS, monophosphoryl lipid A (MPL), produced by removal of the core carbohydrate group and the phosphate from the reducing-end glucosamine, has been described by Ribi, et al., (1986, Immunology and Immunopharmacology of bacterial endotoxins, Plenum Publ. Corp., NY, p 407-419) and has the following structure:

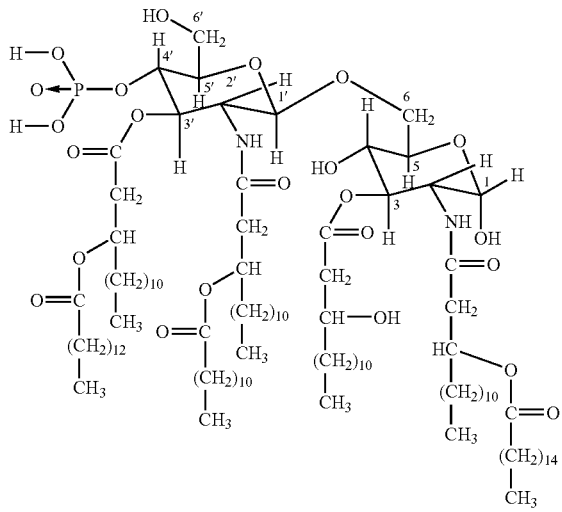

A further detoxified version of MPL results from the removal of the acyl chain from the 3-position of the disaccharide backbone, and is called 3-O-Deacylated monophosphoryl lipid A (3D-MPL). It can be purified and prepared by the methods taught in GB 2122204B, which reference also discloses the preparation of diphosphoryl lipid A, and 3-O-deacylated variants thereof.

A preferred form of 3D-MPL is in the form of an emulsion having a small particle size less than 0.2 µm in diameter, and its method of manufacture is disclosed in WO 94/21292. Aqueous formulations comprising monophosphoryl lipid A and a surfactant have been described in WO9843670A2.

The bacterial lipopolysaccharide derived adjuvants to be formulated in the compositions of the present invention may be purified and processed from bacterial sources, or alternatively they may be synthetic. For example, purified monophosphoryl lipid A is described in Ribi, et al., 1986 (supra), and 3-O-Deacylated monophosphoryl or diphosphoryl lipid A derived from Salmonella sp. is described in GB 2220211 and U.S. Pat. No. 4,912,094. Other purified and synthetic lipopolysaccharides have been described (Hilgers, et al., 1986, Int. Arch. Allergy. Immunol., 79(4):392-6; Hilgers, et al., 1987, Immunology, 60(1):141-6; and EP 0 549 074 B1). A particularly preferred bacterial lipopolysaccharide adjuvant is 3D-MPL.

Accordingly, the LPS derivatives that may be used in the present invention are those immunostimulants that are similar in structure to that of LPS or MPL or 3D-MPL. In another aspect of the present invention the LPS derivatives may be an acylated monosaccharide, which is a sub-portion to the above structure of MPL.

Saponins are taught in: Lacaille-Dubois, M and Wagner H. (1996. A review of the biological and pharmacological activities of saponins. Phytomedicine vol 2 pp 363-386). Saponins are steroid or triterpene glycosides widely distributed in the plant and marine animal kingdoms. Saponins are noted for forming colloidal solutions in water which foam on shaking, and for precipitating cholesterol. When saponins are near cell membranes they create pore-like structures in the membrane which cause the membrane to burst. Haemolysis of erythrocytes is an example of this phenomenon, which is a property of certain, but not all, saponins.

Saponins are known as adjuvants in vaccines for systemic administration. The adjuvant and haemolytic activity of individual saponins has been extensively studied in the art (Lacaille-Dubois and Wagner, supra). For example, Quil A (derived from the bark of the South American tree Quillaja Saponaria Molina), and fractions thereof, are described in U.S. Pat. No. 5,057,540 and "Saponins as vaccine adjuvants", Kensil, C. R., Crit Rev Ther Drug Carrier Syst, 1996, 12 (1-2):1-55; and EP 0 362 279 B1. Particulate structures, termed Immune Stimulating Complexes (ISCOMS), comprising fractions of Quil A are haemolytic and have been used in the manufacture of vaccines (Morein, B., EP 0 109 942 B1; WO 96/11711; WO 96/33739). The haemolytic saponins QS21 and QS17 (HPLC purified fractions of Quil A) have been described as potent systemic adjuvants, and the method of their production is disclosed in U.S. Pat. No. 5,057,540 and EP 0 362 279 B1. Other saponins which have been used in systemic vaccination studies include those derived from other plant species such as Gypsophila and Saponaria (Bomford, et al., Vaccine, 10(9):572-577, 1992).

An enhanced system involves the combination of a non-toxic lipid A derivative and a saponin derivative particularly the combination of QS21 and 3D-MPL as disclosed in WO 94/00153, or a less reactogenic composition where the QS21 is quenched with cholesterol as disclosed in WO 96/33739.

A particularly potent adjuvant formulation involving QS21 and 3D-MPL in an oil in water emulsion is described in WO 95/17210 and is a preferred formulation.

Accordingly in one embodiment of the present invention there is provided a vaccine comprising an influenza antigen preparation of the present invention adjuvanted with detoxified lipid A or a non-toxic derivative of lipid A, more preferably adjuvanted with a monophosphoryl lipid A or derivative thereof.

Preferably the vaccine additionally comprises a saponin, more preferably QS21.

Preferably the formulation additionally comprises an oil in water emulsion. The present invention also provides a method for producing a vaccine formulation comprising mixing an antigen preparation of the present invention together with a pharmaceutically acceptable excipient, such as 3D-MPL.

Additional components that are preferably present in an adjuvanted vaccine formulation according to the invention include non-ionic detergents such as the octoxynols and polyoxyethylene esters as described herein, particularly t-octylphenoxy polyethoxyethanol (Triton X-100) and polyoxyethylene sorbitan monooleate (Tween 80); and bile salts or cholic acid derivatives as described herein, in particular sodium deoxycholate or taurodeoxycholate. Thus, a particularly preferred formulation comprises 3D-MPL, Triton X-100, Tween 80 and sodium deoxycholate, which may be combined with an influenza virus antigen preparation to provide a vaccine suitable for intradermal application.

The invention also provides a method for the prophylaxis of influenza infection or disease in a subject which method comprises administering to the subject intradermally a split influenza vaccine according to the invention.

The invention provides in a further aspect a pharmaceutical kit comprising an intradermal administration device and a vaccine formulation as described herein. The device is preferably supplied already filled with the vaccine. Preferably the vaccine is in a liquid volume smaller than for conventional intramuscular vaccines as described herein, particularly a volume of between about 0.05 ml and 0.2 ml. Preferably the device is a short needle delivery device for administering the vaccine to the dermis.

Suitable devices for use with the intradermal vaccines described herein include short needle devices such as those described in U.S. Pat. Nos. 4,886,499, 5,190,521, 5,328,483, 5,527,288, 4,270,537, 5,015,235, 5,141,496, 5,417,662. Also suitable are jet injection devices which deliver liquid vaccines to the dermis via a liquid jet injector or via a needle which pierces the stratum corneum and produces a jet which reaches the dermis. Jet injection devices are described for example in U.S. Pat. Nos. 5,480,381, 5,599,302, 5,334,144, 5,993,412, 5,649,912, 5,569,189, 5,704,911, 5,383,851, 5,893,397, 5,466,220, 5,339,163, 5,312,335, 5,503,627, 5,064,413, 5,520,639, 4,596,556, 4,790,824, 4,941,880, 4,940,460, WO 97/37705 and WO 97/13537. Also suitable are ballistic powder/particle delivery devices which use compressed gas to accelerate vaccine in powder form through the outer layers of the skin to the dermis. Additionally, conventional syringes may be used in the classical mantoux method of intradermal dministration. However, the use of conventional syringes requires highly skilled operators and thus devices which are capable of accurate delivery without a highly skilled user are preferred.

The influenza vaccine according to the invention is a trivalent influenza vaccine generally comprising three strains of influenza, although it may contain more than three strains. Conventional influenza vaccines comprise three strains of influenza, two A strains and one B strain.

The influenza virus preparations may be derived from the conventional embryonated egg method, or they may be derived from any of the new generation methods using tissue culture to grow the virus. Suitable cell substrates for growing the virus include for example dog kidney cells such as MDCK or cells from a clone of MDCK, MDCK-like cells, monkey kidney cells such as AGMK cells including Vero cells, or any other mammalian cell type suitable for the production of influenza virus for vaccine purposes. Suitable cell substrates also include human cells e.g. MRC-5 cells. Suitable cell substrates are not limited to cell lines; for example primary cells such as chicken embryo fibroblasts are also included.

Traditionally split flu was produced using a solvent/detergent treatment, such as tri-n-butyl phosphate, or diethylether in combination with Tween™ (known as "Tween-ether" splitting) and this process is still used in some production facilities. Other splitting agents now employed include detergents or proteolytic enzymes or bile salts, for example sodium deoxycholate as described in patent no. DD 155 875, incorporated herein by reference. Detergents that can be used as splitting agents include cationic detergents e.g. cetyl trimethyl ammonium bromide (CTAB), other ionic detergents e.g. laurylsulfate, taurodeoxycholate, or non-ionic detergents such as the ones described above including Triton X-100 (for example in a process described in Lina, et al., 2000, Biologicals 28, 95-103) and Triton N-101, or combinations of any two or more detergents.

Further suitable splitting agents which can be used to produce split flu virus preparations include:
1. Bile acids and derivatives thereof including: cholic acid, deoxycholic acid, chenodeoxy colic acid, lithocholic acid ursodeoxycholic acid, hyodeoxycholic acid and derivatives like glyco-, tauro-, amidopropyl-1-propanesulfonic-, amidopropyl-2-hydroxy-1-propanesulfonic derivatives of the aforementioned bile acids, or N,N-bis (3DGluconoamidopropyl) deoxycholamide. A particular example is sodium deoxycholate (NaDOC) which may be present in trace amounts in the final vaccine dose.
2. Alkylglycosides or alkylthioglycosides, where the alkyl chain is between C6-C18 typical between C8 and C14, sugar moiety is any pentose or hexose or combinations thereof with different linkages, like 1->6, 1->5, 1->4, 1->3, 1-2. The alkyl chain can be saturated unsaturated and/or branched.
3. Derivatives of 2 above, where one or more hydroxyl groups, preferably the 6 hydroxyl group is/are modified, like esters, ethoxylates, sulphates, ethers, carbonates, sulphosuccinates, isethionates, ethercarboxylates, quarternary ammonium compounds.
4. Acyl sugars, where the acyl chain is between C6 and C18, typical between C8 and C12, sugar moiety is any pentose or hexose or combinations thereof with different linkages, like 1->6, 1->5, 1->4, 1->3, 1-2. The acyl chain can be saturated or unsaturated and/or branched, cyclic or non-cyclic, with or without one or more heteroatoms e.g. N, S, P or O.
5. Sulphobetaines of the structure R—N,N—(R1,R2)-3-amino-1-propanesulfonate, where R is any alkyl chain or arylalkyl chain between C6 and C18, typical between C8 and C16. The alkyl chain R can be saturated, unsaturated and/or branched. R1 and R2 are preferably alkyl chains between C1 and C4, typically C1, or R1, R2 can form a heterocyclic ring together with the nitrogen.
6. Betains of the structure R—N,N—(R1,R2)-glycine, where R is any alkyl chain between C6 and C18, typical between C8 and C16. The alkyl chain can be saturated unsaturated and/or branched. R1 and R2 are preferably alkyl chains between C1 and C4, typically C1, or R1 and R2 can form a heterocyclic ring together with the nitrogen.
7. N,N-dialkyl-glucamides, of the Structure R—(N—R1)-glucamide, where R is any alkylchain between C6 and C18, typical between C8 and C12. The alkyl chain can be saturated unsaturated and/or branched or cyclic. R1 and R2 are alkyl chains between C1 and C6, typically C1. The sugar moiety might be modified with pentoses or hexoses.
8. Quarternary ammonium compounds of the structure R, —N$^+$ (—R1, —R2, —R3), where R is any alkylchain between C6 and C20, typically C20. The alkyl chain can be saturated unsaturated and/or branched. R1, R2 and R3 are preferably alkyl chains between C1 and C4, typically C1, or R1, R2 can form a heterocyclic ring together with the nitrogen. A particular example is cetyl trimethyl ammonium bromide (CTAB).

The preparation process for a split vaccine will include a number of different filtration and/or other separation steps such as ultracentrifugation, ultrafiltration, zonal centrifugation and chromatography (e.g. ion exchange) steps in a variety of combinations, and optionally an inactivation step, e.g., with formaldehyde or β-propiolactone or U.V. which may be carried out before or after splitting. The splitting process may be carried out as a batch, continuous or semi-continuous process.

Preferably, a bile salt such as sodium deoxycholate is present in trace amounts in a split vaccine formulation according to the invention, preferably at a concentration not greater than 0.05%, or not greater than about 0.01%, more preferably at about 0.0045% (w/v).

Preferred split flu vaccine antigen preparations according to the invention comprise a residual amount of Tween 80 and/or Triton X-100 remaining from the production process, although these may be added or their concentrations adjusted after preparation of the split antigen. Preferably both Tween 80 and Triton X-100 are present. The preferred ranges for the final concentrations of these non-ionic surfactants in the vaccine dose are:
Tween 80: 0.01 to 1%, more preferably about 0.1% (v/v)
Triton X-100: 0.001 to 0.1 (% w/v), more preferably 0.005 to 0.02% (w/v).

The presence of the combination of these two surfactants, in low concentrations, was found to promote the stability of the antigen in solution. It is possible that this enhanced stability rendered the antigen more immunogenic intradermally than previous formulations have been. Such an enhancement could arise from a prevalence of small antigen aggregates or the enhancement of the native conformation of the antigen. It will be appreciated that the invention does not depend upon this theoretical explanation being correct.

In a particular embodiment, the preferred split virus preparation also contains laureth 9, preferably in the range 0.1 to 20%, more preferably 0.1 to 10% and most preferably 0.1 to 1% (w/v).

The vaccines according to the invention generally contain not more than 25% (w/v) of detergent or surfactant, preferably less than 15% and most preferably not more than about 2%.

The invention provides in another aspect a method of manufacturing an influenza vaccine for intradermal application which method comprises:
(i) providing a split influenza virus preparation produced essentially as for a conventional injected (e.g., intramuscular) influenza vaccine and comprising at least one non-ionic surfactant;
(ii) optionally adjusting the concentration of the haemagglutinin and/or the concentration of non-ionic surfactant in the preparation;
(iii) filling an intradermal delivery device with a vaccine dose from the split influenza virus preparation, said dose being a suitable volume for intradermal administration, preferably between about 0.05 ml and 0.2 ml of liquid vaccine.

A further optional step in the method according to this aspect of the invention includes the addition of an absorption-enhancing surfactant such as laureth 9, and/or the addition of an adjuvant such as a non-toxic lipid A derivative, particularly 3D-MPL.

Processes for producing conventional injected inactivated flu vaccines are well known and described in the literature. Such processes may be modified for producing a one-dose intradermal vaccine for use in the present invention, for example by the inclusion of a step for adjusting the concentration of other components e.g. non-ionic surfactants to a suitable % (w/v) for an intradermal vaccine according to the invention. However, the active ingredient of the vaccine, i.e. the influenza antigen can be essentially the same for the conventional intramuscular vaccine and the one-dose intradermal vaccines according to the invention.

Preferably, the vaccine formulations according to the invention do not include formulations that do not meet at least two of the EU criteria for all strains, when administered as a one-dose vaccine.

The invention will now be further described in the following, non-limiting examples.

EXAMPLES

Example 1

Preparation of Split Influenza Vaccine

Each strain for the split vaccine was prepared according to the following procedure.
Preparation of Virus Inoculum
On the day of inoculation of embryonated eggs a fresh inoculum is prepared by mixing the working seed lot with a phosphate buffered saline containing gentamycin sulphate at 0.5 mg/ml and hydrocortisone at 25 µg/ml. (virus strain-dependent). The virus inoculum is kept at 2-8° C.
Inoculation of Embryonated Eggs
Nine to eleven day old embryonated eggs are used for virus replication. Shells are decontaminated. The eggs are inoculated with 0.2 ml of the virus inoculum. The inoculated eggs are incubated at the appropriate temperature (virus strain-dependent) for 48 to 96 hours. At the end of the incubation period, the embryos are killed by cooling and the eggs are stored for 12-60 hours at 2-8° C.
Harvest
The allantoic fluid from the chilled embryonated eggs is harvested. Usually, 8 to 10 ml of crude allantoic fluid is collected per egg. To the crude monovalent virus bulk 0.100 mg/ml thiomersal is optionally added.
Concentration and Purification of Whole Virus from Allantoic Fluid
1. Clarification
The harvested allantoic fluid is clarified by moderate speed centrifugation (range: 4000-14000 g).
2. Adsorption Step
To obtain a $CaHPO_4$ gel in the clarified virus pool, 0.5 mol/L $Na_2HPO_4$ and 0.5 mol/L $CaCl_2$ solutions are added to reach a final concentration of $CaHPO_4$ of 1.5 g to 3.5 g $CaHPO_4$/liter depending on the virus strain.
After sedimentation for at last 8 hours, the supernatant is removed and the sediment containing the influenza virus is resolubilised by addition of a 0.26 mol/L $EDTA-Na_2$ solution, dependent on the amount of $CaHPO_4$ used.
3. Filtration
The resuspended sediment is filtered on a 6 µm filter membrane.
4. Sucrose Gradient Centrifugation
The influenza virus is concentrated by isopycnic centrifugation in a linear sucrose gradient (0-55% (w/v)) containing 100 µg/ml Thiomersal. The flow rate is 8-15 liters/hour.
At the end of the centrifugation, the content of the rotor is recovered by four different fractions (the sucrose is measured in a refractometer):

| | |
|---|---|
| fraction 1 | 55-52% sucrose |
| fraction 2 | approximately 52-38% sucrose |
| fraction 3 | 38-20% sucrose* |
| fraction 4 | 20-0% sucrose |

*virus strain-dependent: fraction 3 can be reduced to 15% sucrose.

For further vaccine preparation, only fractions 2 and 3 are used.

Fraction 3 is washed by diafiltration with phosphate buffer in order to reduce the sucrose content to approximately below 6%. The influenza virus present in this diluted fraction is pelleted to remove soluble contaminants.

The pellet is resuspended and thoroughly mixed to obtain a homogeneous suspension. Fraction 2 and the resuspended pellet of fraction 3 are pooled and phosphate buffer is added to obtain a volume of approximately 40 liters. This product is the monovalent whole virus concentrate.

5. Sucrose Gradient Centrifugation with Sodium Deoxycholate

The monovalent whole influenza virus concentrate is applied to a ENI-Mark II ultracentrifuge. The K3 rotor contains a linear sucrose gradient (0-55% (w/v)) where a sodium deoxycholate gradient is additionally overlayed. Tween 80 is present during splitting up to 0.1% (w/v). The maximal sodium deoxycholate concentration is 0.7-1.5% (w/v) and is strain dependent. The flow rate is 8-15 liters/hour.

At the end of the centrifugation, the content of the rotor is recovered by three different fractions (the sucrose is measured in a refractometer) Fraction 2 is used for further processing. Sucrose content for fraction limits (47-18%) varies according to strains and is fixed after evaluation:

6. Sterile Filtration

The split virus fraction is filtered on filter membranes ending with a 0.2 μm membrane. Phosphate buffer containing 0.025% (w/v) Tween 80 is used for dilution. The final volume of the filtered fraction 2 is 5 times the original fraction volume.

7. Inactivation

The filtered monovalent material is incubated at 22±2° C. for at most 84 hours (dependent on the virus strains, this incubation can be shortened). Phosphate buffer containing 0.025% Tween 80 is then added in order to reduce the total protein content down to max. 250 μg/ml. Formaldehyde is added to a final concentration of 50 μg/ml and the inactivation takes place at 20° C.±2° C. for at least 72 hours.

8. Ultrafiltration

The inactivated split virus material is concentrated at least 2 fold in a ultrafiltration unit, equipped with cellulose acetate membranes with 20 kDa MWCO. The Material is subsequently washed with phosphate buffer containing 0.025% (w/v) Tween 80 and following with phosphate buffered saline containing 0.01% (w/v) Tween.

9. Final Sterile Filtration

The material after ultrafiltration is filtered on filter membranes ending with a 0.2 μm membrane. The final concentration of Haemagglutinin, measured by SRD (method recommended by WHO) should exceed 450 μg/ml.

10. Storage

The monovalent final bulk is stored at 2-8° C. for a maximum of 18 months.

Purity

Purity was determined semiquantitatively by O.D. scanning of Coomassie-stained polyacrylamide gels. Peaks were determined manually. Sample results are given in Table 1:

TABLE 1

| | Viral Proteins (HA, NP, M) % | | | | Other viral and host-cell derived proteins % |
|---|---|---|---|---|---|
| | HA dimer | HA1 + 2 | NP | M | |
| H3N2 | | | | | |
| A/Syd/5/97 | 10.34 | 22.34 | 25.16 | 37.33 | 4.83 |
| A/Nan933/95 | 8.17 | 15.8 | 40.09 | 30.62 | 5.32 |

TABLE 1-continued

| | Viral Proteins (HA, NP, M) % | | | | Other viral and host-cell derived proteins % |
|---|---|---|---|---|---|
| | HA dimer | HA1 + 2 | NP | M | |
| B | | | | | |
| B/Har/7/94 | 5.71[2] | 24.07 | 15.64 | 50 | 4.58 |
| B/Yam/166/98 | 0.68 | 27.62 | 21.48 | 46.02 | 4.2 |
| H1N1 | | | | | |
| A/Tex/36/91 | | 33.42 | 24.46 | 34.33 | 7.79 |
| A/Bei/262/95 | | 32.73 | 35.72 | 27.06 | 4.49 |
| H2N2 | | | | | |
| A/sing/1/57 | 2.8 | 39.7 | 21.78 | 32.12 | 3.6 |

A particular combination of strains includes A/New Caledonia/20/99 (H1N1), A/Panama/20/99 (H3N2) and B/Yamanashi/166/98.

Example 2

Preparation of Vaccine Doses from Bulk Vaccine

Final vaccine is prepared by formulating a trivalent vaccine from the monovalent bulks with the detergent concentrations adjusted as required.

PBS, pH 7.2+/−0.2, Tween 80 and Triton X-100 are mixed to obtain the required final concentrations (PBS 1× concentrated, Tween 80 0.15% and Triton X-100 0.02%). The three following inactivated split virions are added with 10 minutes stirring in between:

15 μg A/New Calcdonia/20/99 ($H_1N_1$)
15 μg A/Panama/20/99 ($H_3N_2$)
15 μg B/Yamanashi/166/98

After 15 minutes stirring pH is adjusted to 7.2+/−0.2.

The dose volume is 500 μl. The doses are filled in sterile ampoules. Immediately before applying the vaccine, 0.1 ml doses are removed from the ampoule using the device for intradermal application.

Example 3

Methods Used to Measure Antibody Responses

1. Detection of Specific Anti-Flu and Total IgA in Human Nasal Secretions by ELISA Collection Method for Human Nasal Secretions An appropriate method is used to collect nasal secretions, for example a classical nasal wash method or a nasal wick method.

After collection and treatment of human nasal secretions, the detection of total and specific anti-FLU IgA is realized with ELISAs e.g:

Capture ELISA for Detection of Total IgA

Total IgA are captured with anti-human IgA polyclonal affinity purified Ig immobilized on microtiter plates and subsequently detected using a different polyclonal anti-human IgA affinity purified Ig coupled to peroxidase.

A purified human sIgA is used as a standard to allow the quantification of sIgA in the collected nasal secretions.

3 references of purified human sIgA are used as low, medium and high references in this assay.

Direct ELISA for Detection of Specific Anti-FLU IgA

Three different ELISAs are performed, one on each FLU strain present in the vaccine formulation.

Specific anti-FLU IgA are captured with split inactivated FLU antigens coated on microtiter plates and subsequently detected using the same different polyclonal anti-human IgA affinity purified Ig coupled to peroxidase as the one used for the total IgA ELISA.

Results—Expression and Calculations

Total IgA Expression

The results are expressed as μg of total IgA in 1 ml of nasal fluids, using a Softmaxpro program.

Specific Anti-Flu IgA Expression

The results are expressed as end-point unit titer, which are calculated as the inverse of the last dilution which gives an $OD_{450}$ nm above the cut off.

The final results of a sample are expressed as follows:

Normalization of the specific response by calculating the ratio between the specific response and the total IgA concentration: end-point unit/μg total IgA (most commonly used calculation method in the literature).

2. Haemagglutination Inhibition (HAI) Activity of Flu-Specific Serum Abs

Sera (50 μl) are treated with 200 μl RDE (receptor destroying enzyme) for 16 hours at 37° C. The reaction is stopped with 150 μl 2.5% Na citrate and the sera are inactivated at 56° C. for 30 min. A dilution 1:10 is prepared by adding 100 μl PBS. Then, a 2-fold dilution series is prepared in 96 well plates (V-bottom) by diluting 25 μl serum (1:10) with 25 μl PBS. 25 μl of the reference antigens are added to each well at a concentration of 4 hemagglutinating units per 25 μl. Antigen and antiserum dilution are mixed using a microtiter plate shaker and incubated for 60 minutes at room temperature. 50 μl chicken red blood cells (RBC) (0.5%) are then added and the RBCs are allowed to sediment for 1 hour at RT. The HAI titre corresponds to the inverse of the last serum dilution that completely inhibits the virus-induced hemagglutination.

We claim:

1. A method for inducing a protective immune response in a human population of at least 18 years old comprising administering intradermally a single dose of a trivalent, split or subunit influenza vaccine antigen preparation using a short needle device, wherein the single dose results in said protective immune response meeting at least one criterion chosen from the group of: (1) a protection rate of >70% in adults of 18-60 years old or of >60% in elderly people of above 60 years old; (2) a seroconversion rate of >40% in adults of 18-60 years old or of >30% in elderly people of above 60 years old; and (3) a conversion factor of >2.5 HI titres in adults of 18-60 years old or of >2.0 HI titres in elderly people of above 60 years old, for each influenza strain.

2. The method according to claim 1, wherein the influenza antigen is egg-derived.

3. The method according to claim 1, wherein the vaccine comprises at least one non-ionic surfactant selected from the group consisting of an octyl-or nonylphenoxy polyoxyethanol, polyoxyethylene sorbitan ester and a polyoxyethylene ether or ester of general formula (I): $HO(CH_2CH_2O)_n$-A-R (I) wherein n is 1-50, A is a bond or —C(O)—, R is $C_{1-50}$ alkyl or phenyl $C_{1-50}$ alkyl.

4. The method according to claim 3, wherein the vaccine comprises a combination of polyoxyethylene sorbitan monooleate (Tween 80) and t-octylphenoxy polyethoxyethanol (Triton X-100).

5. The method according to claim 1, wherein the vaccine further comprises a bile acid or cholic acid, or derivative thereof.

6. The method according to claim 1, wherein the vaccine is provided in a dose volume of between about 0.1 and about 0.2 ml.

7. The method according to claim 1, wherein the vaccine further comprises an adjuvant comprising a combination of cholesterol, a saponin and an LPS derivative.

8. The method according to claim 1, wherein said influenza vaccine antigen preparation is obtained by a process comprising: (i) harvesting virus-containing material from a culture; (ii) clarifying the harvested material to remove non-virus material; (iii) concentrating the harvested virus; (iv) separating whole virus from non-virus material; (v) splitting the whole virus using a suitable splitting agent in a density gradient centrifugation step; and (vi) filtering the product of step (v) to remove undesired materials.

9. A method for inducing a protective immune response in a human population of at least 18 years old comprising administering intradermally a single dose of a trivalent, split or subunit influenza vaccine antigen preparation using a short needle device, wherein said protective immune response meets at least two criteria chosen from the group of: (1) a protection rate of >70% in adults of 18-60 years old or of >60% in elderly people of above 60 years old; (2) a seroconversion rate of >40% in adults of 18-60 years old or of >30% in elderly people of above 60 years old; and (3) a conversion factor of >2.5 HI titres in adults of 18-60 years old or of >2.0 HI titres in elderly people of above 60 years old, for each influenza strain.

10. A method for inducing a protective immune response in a human population of at least 18 years old comprising administering intradermally a single dose of a trivalent, split or subunit influenza vaccine antigen preparation using a short needle device, wherein said protective immune response meets all criteria chosen from the group: (1) a protection rate of >70% in adults of 18-60 years old or of >60% in elderly people of above 60 years old; (2) a seroconversion rate of >40% in adults of 18-60 years old or of >30% in elderly people of above 60 years old; and (3) a conversion factor of >2.5 HI titres in adults of 18-60 years old or of >2.0 HI titres in elderly people of above 60 years old, for each influenza strain.

11. The method according to claim 5, wherein the cholic acid derivative is sodium deoxycholate.

12. The method according to claim 1, wherein the influenza vaccine antigen preparation comprises two A strains and one B strain.

* * * * *